United States Patent
Erkkilä et al.

(10) Patent No.: US 7,330,750 B2
(45) Date of Patent: Feb. 12, 2008

(54) ESTIMATION OF CARDIAC DEATH RISK

(75) Inventors: Jouni Erkkilä, Helsinki (FI); Mikko Kaski, Espoo (FI); Panu Takala, Helsinki (FI)

(73) Assignee: Instrumentarium Corp. (FI)

( * ) Notice: Subject to any disclaimer, the term of this patent is extended or adjusted under 35 U.S.C. 154(b) by 402 days.

(21) Appl. No.: 10/423,474

(22) Filed: Apr. 25, 2003

(65) Prior Publication Data

US 2004/0215090 A1    Oct. 28, 2004

(51) Int. Cl.
    *A61B 5/0402* (2006.01)
(52) U.S. Cl. ................................................. 600/509
(58) Field of Classification Search ......... 600/509–519
    See application file for complete search history.

(56) References Cited

U.S. PATENT DOCUMENTS

| | | | |
|---|---|---|---|
| 5,265,617 A * | 11/1993 | Verrier et al. ............... | 600/517 |
| 5,713,367 A * | 2/1998 | Arnold et al. ............... | 600/517 |
| 5,769,793 A | 6/1998 | Pincus et al. | |
| 6,067,466 A * | 5/2000 | Selker et al. ............... | 600/513 |
| 6,169,919 B1 | 1/2001 | Nearing et al. | |
| 6,272,377 B1 * | 8/2001 | Sweeney et al. ............ | 600/515 |
| 6,308,094 B1 | 10/2001 | Shusterman et al. | |
| 6,487,442 B1 | 11/2002 | Wood | |
| 6,656,125 B2 * | 12/2003 | Misczynski et al. ......... | 600/508 |
| 6,665,559 B2 * | 12/2003 | Rowlandson ............... | 600/515 |
| 6,934,577 B2 | 8/2005 | Hutten et al. | |
| 6,993,377 B2 | 1/2006 | Flick et al. | |
| 6,821,256 B2 | 11/2006 | Ackermann et al. | |
| 6,968,227 B2 | 11/2006 | MacAdam et al. | |
| 2002/0138012 A1 | 9/2002 | Hodges et al. | |
| 2003/0114763 A1* | 6/2003 | Reddy et al. ............... | 600/483 |

OTHER PUBLICATIONS

S.G. Priori et al., "Task Force on Sudden Cardiac Death of the European Society of Cardiology", Task Force Report, European Heart Journal (2001) 22, 1374-1450.
ACC/AHA Practice Guidelines, "1999 Update: Guidelines for the Management of Patients with Acute Myocardial Infarction—Part IV", 1999, pp. 1-29.

(Continued)

*Primary Examiner*—Scott M. Getzow
(74) *Attorney, Agent, or Firm*—Andrus, Sceales, Starke & Sawall, LLP

(57) ABSTRACT

The invention relates to a method and apparatus for predicting a sudden heart abnormality for an individual patient. In order to provide a prediction mechanism that is suitable for acute care, three sub-indices are determined based on medical data obtained from the patient. The first sub-index indicates the level of deterministic chaos in the heart rate variability of the patient, the second sub-index indicates the energy level in the myocardium of the patient, and the third sub-index indicates the degree of ventricular arrhythmia of the patient. Based on the first, second, and third sub-indices, at least one overall risk index is then determined, the overall risk index indicating the risk level of a sudden heart abnormality for the patient.

16 Claims, 4 Drawing Sheets

OTHER PUBLICATIONS

Fractal Mechanisms in Neural Control: Human Heartbeat and Gait Dyamics in Health and Disease, Peng C-K, http://www.physionet.org/tutorials/fmnc.

"Heart Rate Dynamics in Patients with Stable Angina Pectoris and Utility of Fractal and Complexity Measures", Makikallio et al., Am. J. Cardiology 1998 81(1):27-31.

"Power-law relationship of heart rate variability as a predictor of mortality in the elderly", Huikuri et al., Circulation: 97(20):2031-6.

"Non-linear Heart rate Variability and Risk Stratification in Cardiovascular Disease", Stein et al., Indian Pacing and Electrophysiology Journal, 5(3): 210-220 (2005).

* cited by examiner

ESTIMATION OF CARDIAC DEATH RISK

BACKGROUND OF THE INVENTION

1. Field of the Invention

The present invention relates generally to a method and apparatus for prognosticating unexpected cardiovascular disorders, such as cardiac arrests of patients having or suspected of having one or more cardiac diseases. The method of the invention involves calculating an index indicating the risk of a sudden cardiac death. Below, this index is termed the Sudden Cardiac Death Risk Index (SCDRI).

2. Description of the Related Art

State-of-art physiologic monitors provide a large variety of different parameters alerting the clinical and nursing staffs to lethal events of patients. However, the algorithms for calculating each parameter monitored require time from the onset of the lethal event, such as ventricular fibrillation (VF), Torsades de Pointes (TdP), or ventricular tachycardia (VT), before the alarm is given. Thus, there is typically a delay before the clinical staff is alerted to arrange the necessary therapy, e.g. defibrillation during lethal events with the patients. In the worst case, when only the electrocardiogram (ECG) signal is monitored, the delay may be as high as 60 seconds before the relevant alarm of a lethal event is given. At present, the nursing staff has the responsibility of making the prognosis based on their experience in interpreting the massive amount of parameters in acute care (acute care refers to a level of health care in which a patient is treated for a brief but severe episode of illness, for conditions that are the result of disease or trauma, or during recovery from surgery). Given the facts that every minute from the onset of a cardiac arrest reduces the survival chances of the patient by 7 to 10 percent and that irreversible damage starts to occur within 4 to 6 minutes, the experience of the nursing staff is vital.

Clinical studies have shown the non-linear behavior of heart function and control mechanisms. Several parameters have been identified that indicate the baro-reflex sensitivity (BRS) and the dynamics of the autonomic and vagal control mechanisms of the heart. Some of these parameters, such as heart rate variability (HRV), have been studied and proved to have value in predicting a cardiac arrest. For example, depressed function of the cardiovascular control system is seen as decreased chaos in the HRV. This means that there are less chaotic but more periodic frequency components in the HRV. In other words, a healthy heart rhythm is chaotic showing a fractal form, which is broken by an abnormality or disease.

One method based on the detection of chaos is disclosed in U.S. Pat. No. 5,769,793. In this method, a quantity called "approximate entropy" is determined based on the medical data measured, the "approximate entropy" indicating the degree of chaos in the behavior of the human body, for example. The method may be used, for example, in the analysis of electrocardiograph data, such as beat-to-beat heart rate data derived from an ECG signal.

One drawback with the above-mentioned method is that it studies the entire behavior of the cardiovascular control mechanism, but not the local disorders of the myocardium. If the patient suffers from poor perfusion, adequate oxygenation and correct energy balance cannot be maintained for the myocardium, which may lead to cardiac ischemia and to an acute infarct. In order to arrange an adequate therapy and to avoid lethal injuries in the heart, it is thus crucial to have knowledge of the current local processes in the myocardium. A reliable indirect method for measuring the myocardial oxygenation is the examination the ST segment level, for example, of the ECG of the patient.

In this connection, reference is made to FIG. 1 that shows one cycle of an ECG signal. As is commonly known, and also shown in the figure, the waves of the ECG signal (i.e. the depolarisation and repolarisation events in the heart) are named alphabetically from P to U. Modern ECG devices use digital signal processing to analyze the shape and the consistency of, and the durations between these waveforms. In addition to the ST segment level, the examination of the T wave morphology and the QT duration are also highly valuable in estimating the energy balance and the ion pump function of the myocardium and its cells, i.e. local disorders of the myocardium. Proarrhythmia drugs may prolong the QT duration, which has been found to increase the risk of TdP and VF, and sudden death. Furthermore, lack of oxygen and an electrolyte imbalance may cause ventricular arrhythmias and bundle branch blocks. These life-threatening phenomena can be seen on the ECG as changes in the ST segment level and in the T wave amplitude. Detection of rhythm and conduction abnormalities, such as bundle branch blocks, require measurement of P, QRS, and T wave intervals and amplitudes. This can be implemented by commercially available interpretation algorithms, such as the Glascow Royal Infirmary program. Continuous monitoring and comparison of the ECG reveals the propagation of abnormal events.

Many scientific studies have also been published, which aim to find a diagnostic method for identifying the patients with the risk of a sudden cardiac death. One of such studies is disclosed in US Patent Application 2002/0138012 that discloses a method for identifying the patients with increased risk of having an episode of Sudden Cardiac Death syndrome (SCD) and thus in the need of receiving an implantable cardioverter-defibrillator (ICD) to reduce the risk. In these methods, the data is collected by specific diagnostic devices, such as ECG cards or ambulatory Holter devices featuring 24 hours monitoring, ECG storage and off-line analysis. The collected and stored data is analyzed off-line by separate computers.

These screening systems have not been designed for acute care, where continuous and real-time monitoring is a basic and fundamental requirement.

It is the objective of the invention to provide a mechanism for alerting in advance of the onset of a cardiac event, such as cardiac arrest, of a patient in acute care.

SUMMARY OF THE INVENTION

The objective of the present invention is to bring about a new solution for predicting the onset of a cardiovascular disorder, such as a cardiac arrest. Other objectives of the invention are to improve the prediction ability of the methods based on detection of chaos in the HRV, and to provide a solution that is particularly suitable for estimating cardiac death risk in acute care.

In the present invention, three different indices describing the status of the heart are determined and combined to define at least one overall risk index. The three indices, each describing the current status of the heart from a different aspect, are termed the chaos index, the energy balance index, and the electrophysiological index according to the aspects to which they relate. The chaos index indicates the level of chaos of heart rate variability, which, in turn, indicates whether the cardiovascular control system operates in an adequate manner. The energy balance index in turn indicates the current energy level of the myocardium, or, which is logically the same thing, the current deviation from a typical (i.e. normal) energy balance of the myocardium. The electrophysiological index is a measure of the degree of ventricular arrhythmia, and possibly also of conduction abnormalities in the heart. These three indices are also termed sub-indices in this context.

The sub-indices are submitted to a combinatory algorithm that combines them in order to define one or more overall risk indices. If only one overall risk index is used, it is termed the Sudden Cardiac Death Risk Index (SCDRI) in this context. Thus, in the present invention the prediction ability of a chaos-based method is improved by complementing a predictor based on the chaos method by two other predictors indicating local disorders in the heart. As the clinical personnel may, however, want to ensure the origin of the alerting risk values or the trend of the SCDRI, the said complementing is implemented so that the different predictors (sub-indices) may be reviewed separately. By combining large amounts of physiological information, the combined and trended SCDRI of the invention reduces the treatment or resuscitation delays and facilitates the decision-making in preparing the treatment.

Thus one aspect of the invention is providing a method for predicting cardiovascular disorders for an individual patient, the method comprising the steps of:

determining a first sub-index indicating the current level of chaos in heart rate variability of a patient;

determining a second sub-index indicating the current energy level in the myocardium of the patient;

determining a third sub-index indicating the current degree of arrhythmia of the patient; and based on the first, second, and third sub-indices, determining at least one overall risk index, the overall risk index indicating a risk level of a cardiovascular disorder for the patient.

The invention provides a mechanism that allows the clinical and nursing staff to be alerted in advance of the onset of a lethal cardiac event, thereby substantially reducing the treatment or resuscitation delay. Since these delays are critical in view of the survival of the patient, the mechanism of the invention significantly improves the survival chances of the patient and also reduces the irreversible damage caused by cardiac arrests. Furthermore, the invention relieves the burden of the nursing staff, as they can select a proper treatment before irreversible damage to the patient, and thereby shorten the length of stay of the hospitalized patient.

A further advantage of the system of the invention is that it utilizes typical bedside signal parameters and algorithms for forming the risk index. Therefore, known components can be utilized to a great extent, thereby facilitating the implementation of the system.

Another aspect of the invention is that of providing a system for predicting a cardiovascular disorder for an individual patient, the system comprising:

measurement means for obtaining medical data from an individual patient, the medical data including ECG data;

first calculation means for determining a first sub-index based on the medical data, the first sub-index indicating the current level of chaos in heart rate variability of a patient;

second calculation means for determining a second sub-index based on the medical data, the second sub-index indicating the current energy level in the myocardium of the patient;

third calculation means for determining a third sub-index based on the medical data, the third sub-index indicating the current degree of arrhythmia of the patient; and fourth calculation means for determining at least one overall risk index based on the first, second, and third sub-indices, the overall risk index indicating a risk level of a cardiovascular disorder for the patient.

In one embodiment of the invention, the determination of the sub-indices is based on an ECG signals only.

Other parameters than those derivable from ECG signals, may additionally be utilized in determining one or more of the sub-indices. In one embodiment of the invention, for example, the blood pressure of the patient is utilized for determining myocardial contractility, which is related to the energy balance of the myocardium.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 2 to 7 in the appended drawings, wherein.

DETAILED DESCRIPTION OF THE INVENTION

Below, the invention is disclosed in the context of monitoring a hospitalized patient in acute care.

Figure 2:
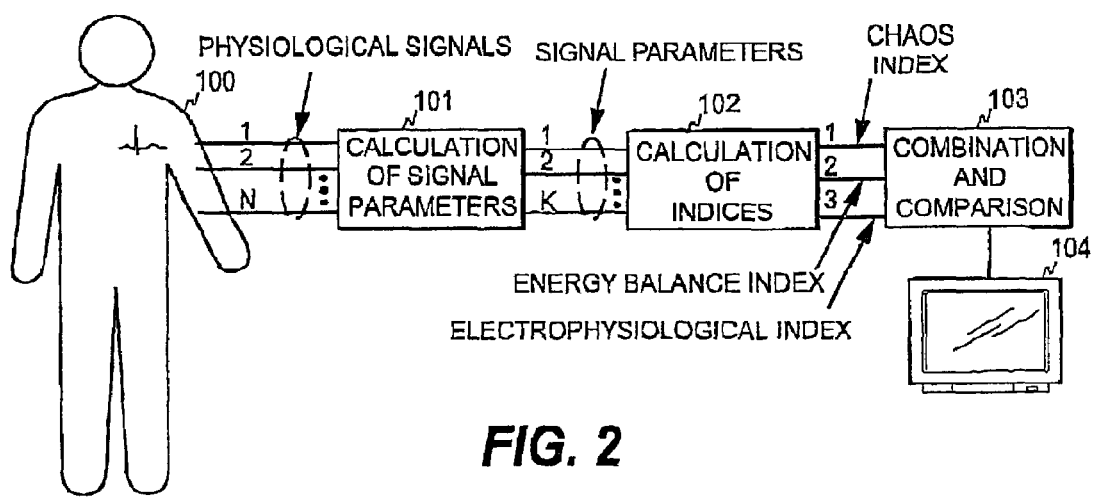
FIG. 2 is a logical presentation of the measurement system of the invention.

FIG. 2 is a logical presentation of the measurement system of the invention. In the system of the invention, N (N=1, 2, 3, . . . ) electrodes and sensors are attached to patient 100, the electrodes and sensors providing a set of physiological signals. This set of signals is supplied to a first processing stage 101 where a set of signal parameters is calculated on the basis of the said signals. It is assumed in the figure that this set includes K signal parameters. The signal parameters are supplied to a second processing stage 102 where three sub-indices are determined based on the signal parameters, the sub-indices being: a chaos index, an energy balance index, and an electrophysiological index.

The physiological signals and the signal parameters may be divided into three categories in accordance with the sub-indices: the signals and signal parameters utilized to determine the chaos index, the signals and signal parameters utilized to determine the energy balance index, and the signals and signal parameters utilized to determine the electrophysiological index. However, it is also possible that one or more signals or signal parameters are utilized for the determination of more than one of said sub-indices.

The said three sub-indices are submitted to a third processing stage 103 in which an overall risk index (SCDRI) is calculated based on the sub-indices. An initial SCDRI is formed in the beginning of the monitoring period, for example during the first 15 minutes of the monitoring period, based on the initial status of the patient. During the monitoring period, more data is collected and the SCDRI is updated based on fresh data. Based on the comparison of subsequent SCDRI values, it is then decided in the third processing stage whether an alarm of increased risk of a lethal condition is given or not. The alarms are displayed on a separate display unit 104 displaying the results of the risk index calculation.

As discussed below, external information, such as laboratory data of the patient, may further be utilized in the process of the invention, in addition to the data measured directly from the patient.

Figure 3:
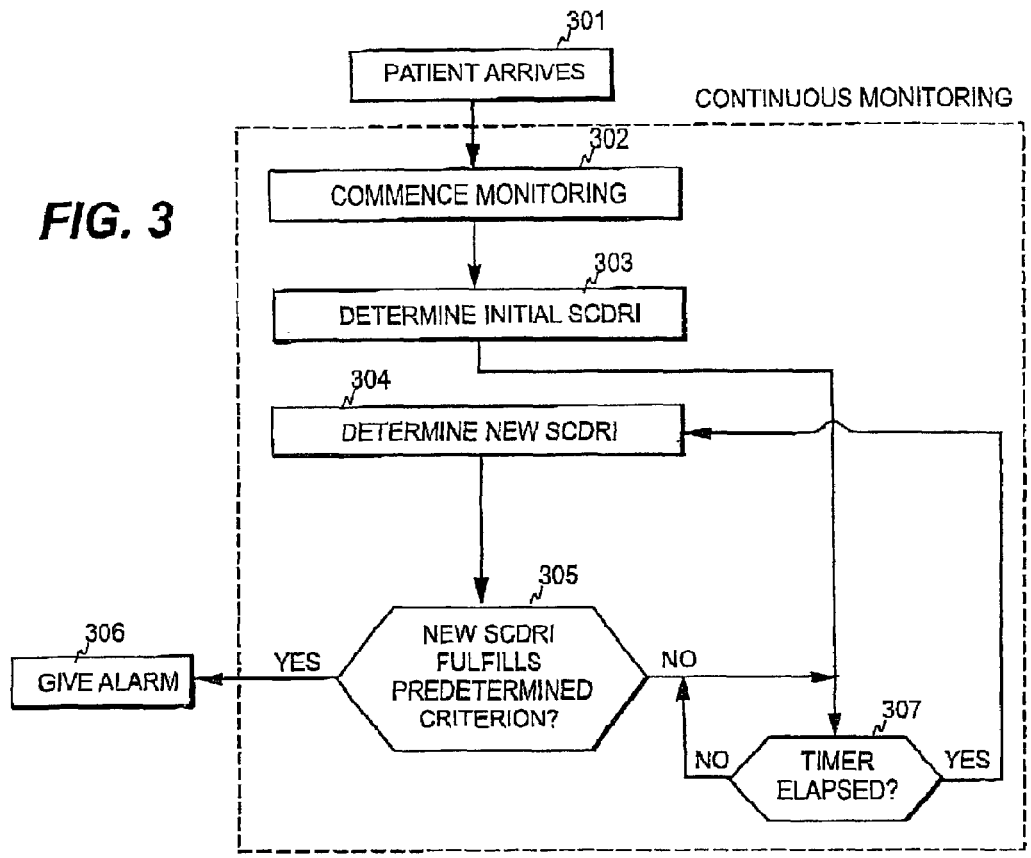
FIG. 3 is a flow diagram illustrating the operation of the system of the invention.

FIG. 3 is a flow diagram illustrating the operation of the system of FIG. 2. The monitoring is started at once when the patient arrives at the hospital (steps 301 and 302). As mentioned above, an initial SCDRI is formed in the beginning of the monitoring period, the initial SCDRI serving as a reference for upcoming measurements (step 303). Depending on the value of the initial SCDRI, at least one alarm criterion may be set for the patient. This criterion may be a threshold value for the SCDRI, for example, which determines when the nursing staff is alerted of the onset of a lethal event. Thus, the alarm threshold typically depends on the value of the initial SCDRI, and it may be set manually or automatically.

A new SCDRI is then determined periodically, according to the situation of the patient, for example every 10 minutes, beat by beat, or even more frequently (steps 307 and 304). The period between two successive SCDRI determinations may be dependent on the rate of change of the SCDRI. It is to be noted here that although the determination of the SCDRI is periodic, the measurement data on which the determination is based is collected continuously. When a new SCDRI has been calculated, it is examined whether the new SCDRI meets the above-mentioned at least one alarm criterion (step 305). This step typically includes the comparison of the new SCDRI with the reference or threshold value set at step 303 to detect whether the SCDRI has reached the alarm threshold. If this is so, an alarm is given (step 306). Otherwise a new SCDRI value is calculated after a predetermined period defined by a timer, for example, and the new SCDRI value is again compared with the predetermined at least one alarm criterion.

Figure 4:
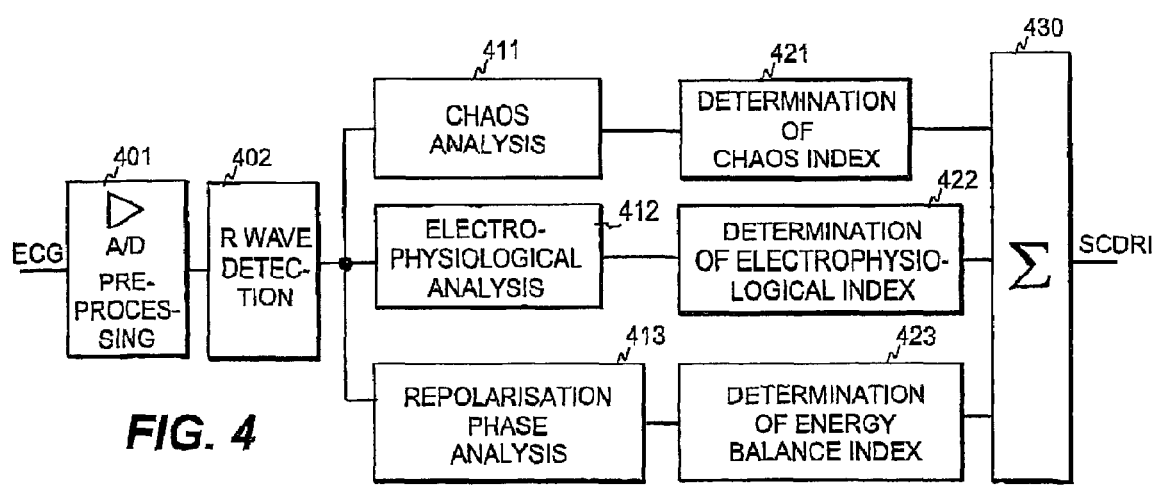
FIG. 4 illustrates one embodiment of the invention.

FIG. 4 illustrates an embodiment of the invention that relies on ECG data only. Although several ECG signals are normally utilized, it is assumed here, for the sake of simplicity, that only one ECG signal originates from the patient. In practice, the ECG is typically measured by a known 3, 5, or 10 electrode configuration, giving 1, 3, or 8 signals, respectively. The electrode configurations may follow the Einthoven or modified Mason-Likar configurations, for example. By using more signals, the accuracy of the system can be improved, since the information carried by several signals can be taken into account.

Figure 1:
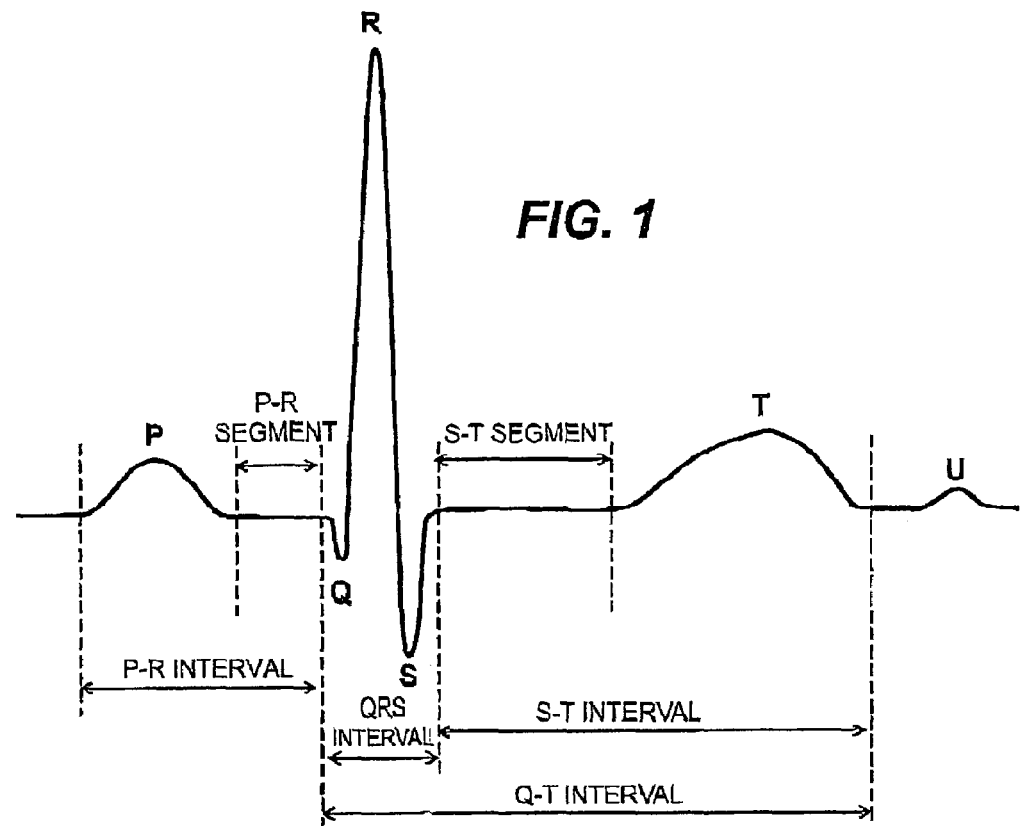
FIG. 1 illustrates an ECG signal of one cardiac cycle.

The ECG signal is first supplied to a preprocessing stage 401 where the signal is amplified, sampled, converted into digitized format and pre-processed. The digitized signal is then submitted to an R wave detection unit 402, which detects the R waves (cf. FIG. 1) of the ECG signal in order to "synchronize" the samples with the actual ECG signal. The ECG signal is then supplied to three different branches, each determining one of the sub-indices. In the first branch, a chaos analysis is performed on the ECG signal at an analysis stage 411 and a chaos index is determined based on the analysis in a first sub-index determination unit 421. In the second branch, an electrophysiological analysis is first performed on the ECG signal at an analysis stage 412 and an electrophysiological index is then determined based on the analysis in a second sub-index determination unit 422. In the third branch, an analysis is first performed on the repolarisation phase of the ECG signal at an analysis stage 413, and an energy balance index is then determined based on the analysis in a third sub-index determination unit 423.

The SCDRI is then calculated in a combinatory unit 430 based on the three sub-indices. As discussed below, a sub-index may be obtained directly from the corresponding analysis stage, i.e. a separate unit/stage is not necessarily needed for calculating the sub-index based on the respective analysis. Since each of the three sub-indices independently reflects the risk of a sudden cardiac death, the overall risk index may be calculated as a weighted sum of the sub-indices in the combinatory unit. The weights of the sub-indices may be defined according to known risk stratifications relating to the parameters used for calculating the sub-indices. For example the European Society of Cardiology has published a Task Force Report for Sudden Cardiac Death (SCD), the report being available at http://www.escardio.org/scinfo/Guidelines/suddendeath.pdf (visited in April 2003). On page 1387, the report discloses a summary of SCD evidence, which can be used for evaluating the mutual importance of the weights.

Instead of one overall risk index, several overall risk indices may be determined in the combinatory unit. This may be implemented, for example, by calculating each overall risk index as a weighted sum of the sub-indices but with different weights.

The chaos analysis may consist of a known HRV (Heart Rate Variability) analysis based on recording the R-R intervals, since the chaos level of the cardiovascular control system can be seen in the HRV. The HRV analysis is based on known HRV analysis techniques, such as the detrended fluctuation method, the approximate entropy method, the power-law relationship analysis of heart rate dynamics, or the Kolmogorov entropy method. These analyses typically output a numerical value that can be directly used as the chaos index.

The electrophysiological analysis comprises at least an arrhythmia analysis that typically outputs the number of abnormal ventricular beats in a time unit, such as in a minute. The electrophysiological index can therefore be proportional to this number, if no other analyses than the arrhythmia analysis are utilized. The arrhythmia analysis may be based on a method called template matching, for example. In methods like this, QRS complexes are detected and templates are formed of similar QRS complexes. Each template and the beats belonging to it are labeled as normal, ventricular or paced. Another known method that can be used for the arrhythmia analysis is the QRS feature discrimination method.

The repolarisation phase analysis utilizes the information over the entire repolarisation phase of the heart, i.e. from the S wave ahead. This analysis includes the examination of the T wave morphology, which gives information of T wave parameters such as the T wave area and amplitude. The analysis may further indicate parameters such as QT time, $QT_c$ time, and ST segment level.

Late potentials and the amplitudes of the U waves may also be utilized. The signal parameters defined in the repolarisation phase analysis are termed the repolarisation parameters in this context. The energy balance index is calculated as a weighted sum of at least some of the repolarisation parameters, for example. It is also possible to use scoring methods based on the recommendations and clinical evidence according to the Guidelines of the American College of Cardiology (ACC) and the American Heart Association (AHA).

Figure 5:
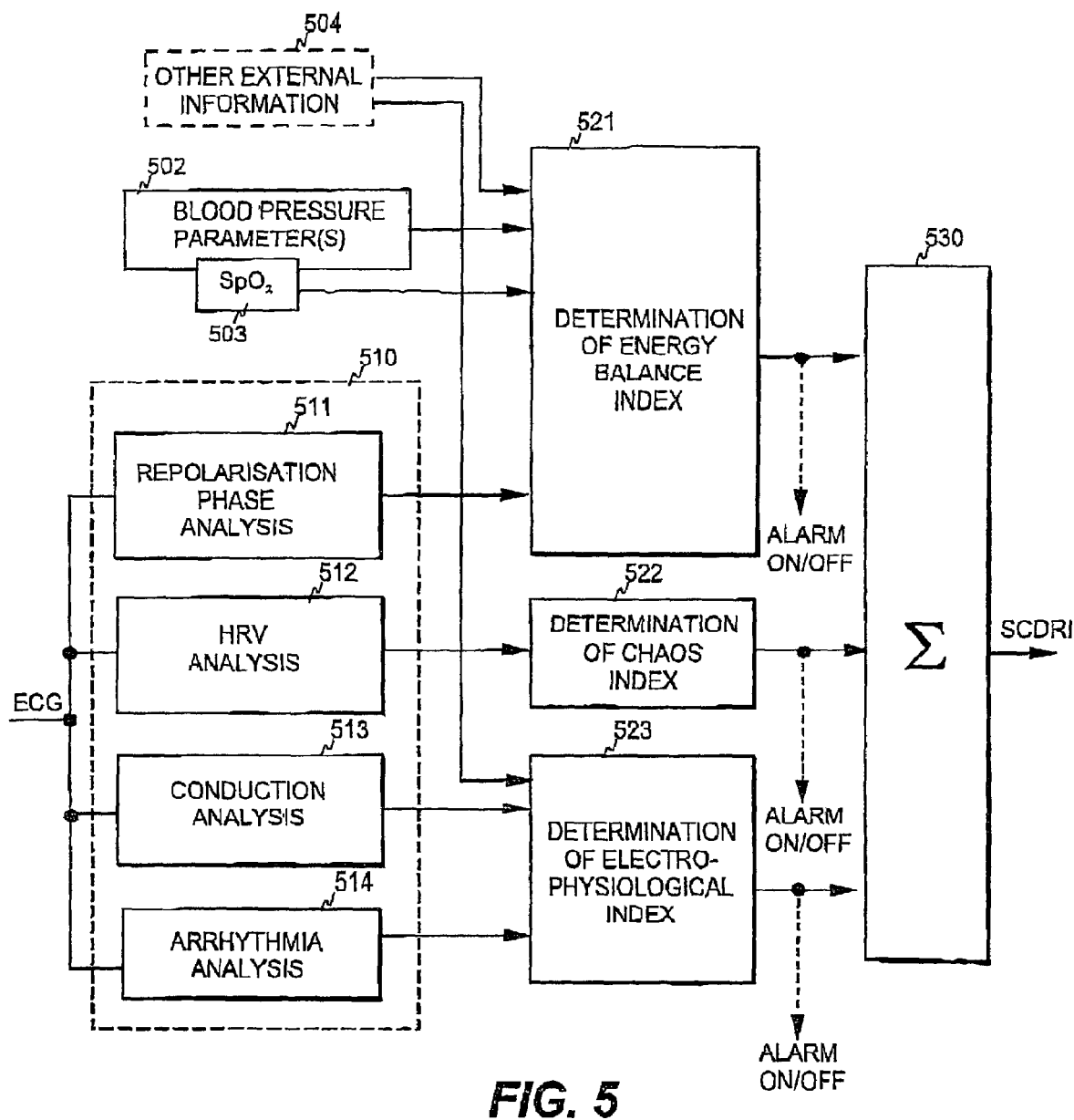
FIG. 5 illustrates another embodiment of the invention.

FIG. 5 illustrates another embodiment of the invention, in which external information is utilized, in addition to the ECG signal(s), and in which a conduction analysis is utilized, in addition to the arrhythmia analysis, for determining the electrophysiological index. The ECG signal is supplied to an analysis block including four different analysis units 511 to 514. The repolarisation phase analysis unit 511 and the chaos analysis unit 512 may be similar as the corresponding units 413 and 411, respectively, in FIG. 4. However, the electrophysiological analysis unit comprises two parallel units, an arrhythmia analysis unit 514, which may be similar to the corresponding unit 412 in FIG. 4, and a conduction analysis unit 513, where conduction abnormalities, such as SA (Sino-Atrial exit), AV (Atrio-Ventricular), and IV (IntraVentricular) blocks are identified. The conduction analysis gives information of the local disorders of the myocardium, and its typical output indicates the number of abnormal ventricular beats, which are due to abnormal conduction, in a time unit. The electrophysiological index calculated at stage 523 can therefore be directly proportional to the weighted sum of the numbers received from the arrhythmia analysis and from the conduction analysis.

The determination of the sub-indices may further utilize other measurements than the ECG measurement. This is discussed below with reference to FIG. 5.

Firstly, one or more parameters 502 describing the arterial blood pressure of the patient may be taken into account when determining the energy balance index. These parameter(s) may be measured invasively or non-invasively. For example, systolic, diastolic, and mean pressures, which are indications of the workload of the heart, may be measured. Furthermore, the slew rate of the pressure signal (dP/dt) may be used as a parameter, since it is an indication of the myocardium contractility. Therefore, parameters relating to the arterial blood pressure may be utilized in calculating the energy balance index.

Secondly, a pulse oximeter may also be utilized for providing an indication of the arterial blood oxyhemoglobin saturation ($SpO_2$). The $SPO_2$ value 503 may be utilized in calculating the energy balance index. The $SPO_2$ value can be taken into account by using an appropriate coefficient in front of the weighted sum that forms the energy balance index in the absence of the $SPO_2$ measurement. If the $SPO_2$ value is normal, the said coefficient equals to one, and if the $SPO_2$ value drops, the coefficient increases, thereby indicating increased risk. In this way, the energy balance index may indicate an increased risk even though the $SPO_2$ value is normal. For example oxygenation therapy given to the patient results in a normal $SPO_2$ value, but in spite of that the ST segment level and the T waves show abnormal values, which is strong evidence of ischemia being present in the myocardium.

Thirdly, it is also possible to utilize information 504 that is measured off-line or derived otherwise indirectly, such as laboratory results. This information may include electrolyte values (e.g. $Na^+$, $K^+$, $Cl^-$, $Ca^{2+}$, $Mg^{2+}$), blood gas values ($pO_2$, $pCO_2$), pH values, and enzymes (e.g. Lactate), for example. The values can be supplied to the system manually, or the system can read them from the hospital laboratory information system (HLIS) via a local area network. The electrolytes support the derivation of the electrophysiological index, while the blood gas, pH and enzymes values support the derivation of the energy balance index. The scoring and summing of the values with the energy balance and electrophysiological indices is one possible method for utilizing the laboratory results. The normal concentrations of said parameter values are known and thus they can be utilized by a scoring method, based on the ACC/AHA Clinical Guidelines for cardiac diseases. (ACC/AHA Practice Guidelines, 1999 Update: Guidelines for the Management of Patients with Acute Myocardial Infarction, Myocardial Infarction—-Part IV, available on-line at http://www.americanheart.org/presenter.jhtml?identifier=2865 (visited in April, 2003)).

Figure 6:
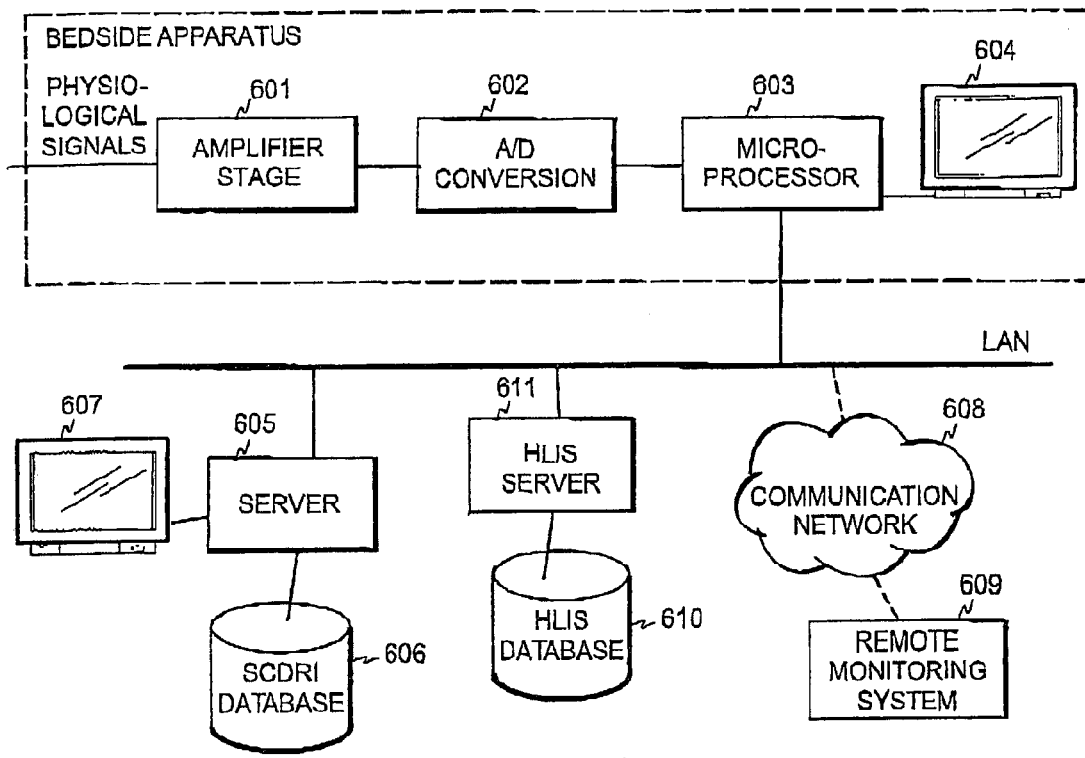
FIG. 6 illustrates the implementation of the system of the invention in a hospital environment.

FIG. 6 illustrates one embodiment of the system according to the invention, in which a centralized server may serve one or more bedside devices. The physiological signals obtained from the different sensors attached to the patient are supplied to an amplifier stage 601, which amplifies the signals before they are sampled and converted into a digitized format in an A/D converter 602. The digitized signals are supplied to a microprocessor 603, which calculates the signal parameters, i.e. in this embodiment the amplifier stage, the A/D converter, and the microprocessor form the first processing unit shown in FIG. 1. The microprocessor may be provided with a monitor 604 for displaying the signal parameters and/or the results of the SCDRI calculation at the patient.

The microprocessor is further connected to a local area network (LAN) of the hospital for transferring the signal parameters to a centralized server 605. In this embodiment the server forms the second and third processing units that calculate the indices based on the signal parameters received from the bedside apparatus. The server is provided with a database 606 holding the reference data and the data related to previous measurements (i.e. to previously measured signal parameters). The microprocessor sends the set of signal parameters periodically to the server, which then calculates the three sub-indices, the overall risk index and compares the overall risk index with the reference data stored in the database. The results may be shown on a display 607 connected to the server and they may further be sent through the LAN to be displayed on the bedside monitor 604. A remote monitoring system 609 may further be connected to the LAN through a communication network 608. The alarm may be given at desired points of the system.

If laboratory results are utilized, they may be retrieved from a HLIS database 610 that may be in connection with the above-mentioned server 605 or, as is shown in FIG. 6, in connection with a separate HLIS server 611 connected to the LAN.

Figure 7:
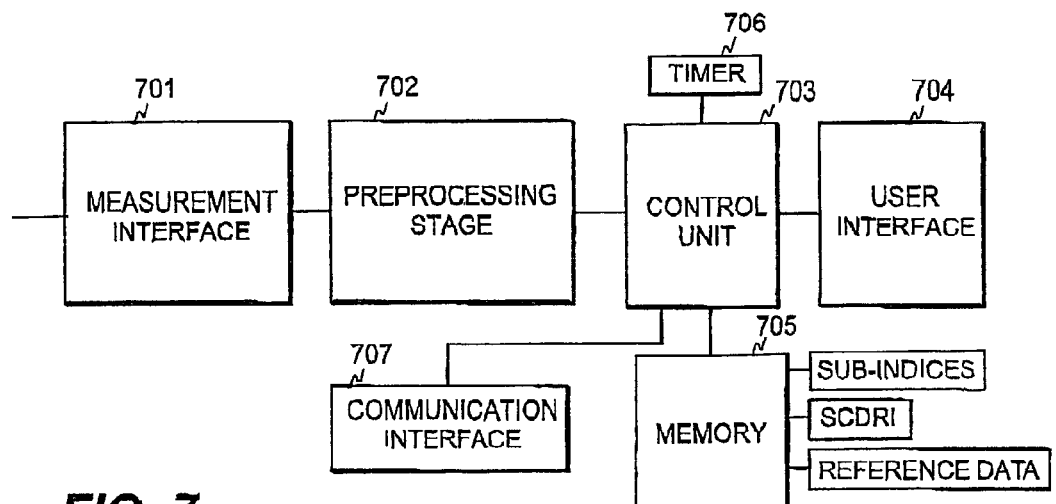
FIG. 7 illustrates the apparatus of the invention.

FIG. 7 illustrates an apparatus of the invention, which may be a bedside monitor or an ambulatory monitor. The different sensors attached to the patient are connected to a measurement interface 701. The physiological signals are supplied to a preprocessing stage 702, which amplifies the signals before they are sampled and converted into digitized format in an A/D converter included in the preprocessing stage. The digitized signals are connected to a control or processor unit 703, which performs the estimation according to the invention. For this purpose, the control unit is provided with a memory 705 that stores the information needed to determine the sub-indices and at least one overall risk index, and with timer means 706 for periodically calculating the SCDRI. Thus, in this case the determination of the indices is performed in a centralized manner in one processing unit 703. A user interface 704, which is connected to the control unit through data and control busses, typically includes a display and a control board through which the nursing staff is able to operate the apparatus. The user interface further includes an alarm device for giving a visual and/or audio alarm to the nursing staff. The device may further be provided with a communication interface 707 through which the apparatus may communicate with other devices.

As disclosed in the following table, the invention may utilize various known analyses and physiological parameters.

| Index | Parameter | Method |
|---|---|---|
| Chaos Index ("CI") | R—R interval | Heart Rate Variability and Chaos analysis: Detrended fluctuation method Approximate entropy Power law relationship analysis Two dimensional vector analysis Kolmogorov entropy |
| Energy Balance Index (EBI) | ST segment | ST segment level 60-80 msec after J point ST segment slope |
| | T wave morphology | T wave amplitude and vector T wave duration T wave/QRS wave amplitude ratio |
| | QT duration | QT duration |
| | Arterial blood pressure | dP/dt slew rate |
| | Pulse oximeter | $SpO_2$ |
| | Blood oxygenation: pO2, pCO2, H | Laboratory analysis |
| | Enzymes and cardiac markers | Laboratory analysis |
| Electrophysiological Index (EI) | ECG signals | ECG interpretation analysis P wave recognition QRS wave morphology QRS axes and vectors T wave morphology P, QRS, T waves and their respective durations Conduction analysis such as bundle branch blocks Arrhythmia analysis QRS morphology PVC minute rate Sustained and non-sustained V-TAC events |
| | Electrolytes: $Na^+$, $K^+$, $Cl^-$, $Mg^{2+}$, | Laboratory analysis |

Although the method suits well for acute care, the method can be used in respective care areas and applications. For example, the invention may be used in care areas such as ambulatory care, nursing homes and in home care. If the patient is mobilized and able to move short distances, the patient may carry a small monitoring device that measures the physiological parameters, such as the ECG, SpO2 and blood pressure. The monitoring device may feature a short-range radio transmitter, such as a Bluetooth transmitter (cf. interface 707 in FIG. 7). The radio signals may be received at a computer that performs the calculation of the SCDRI in the above-described manner. The SCDRI data can be transmitted to the responsible clinical personnel via the Internet or a proprietary communication network, for example.

The parameter measurement and the SCDRI determination may also be performed in a single portable device carried by the patient. The SCDRI data can then be transmitted to the responsible clinical staff by a mobile phone connected to the device. This system enables the patient's entire mobilization without range limitations. As the patient's mobile phone can be located by the state-of-art location methods, the treatment can be arranged to the patient by existing emergency services, without any specific back-up organizations.

Although the invention was described above with reference to the examples shown in the appended drawings, it is obvious that the invention is not limited to these, but may be modified by those skilled in the art without departing from the scope and spirit of the invention. For example, the measurement devices by which the medical data (i.e. the physiological signals) are obtained from the patient may include various types of known devices or measurement methods. Furthermore, instead of using continuous values, the calculation of at least some of the sub-indices may utilize logical values. In other words, a sub-index may just indicate whether the corresponding level or degree is normal or abnormal.

The invention claimed is:

1. A method providing a composite, multiple component index for assessing a current state of a patient's heart to evaluate associated cardiac health risks, the method comprising the steps of:
    determining a first sub-index indicating the current level of chaos in heart rate variability of a patient;
    determining a second sub-index indicating the current energy level in the myocardium of the patient;
    determining a third sub-index indicating the current degree of arrhythmia of the patient; and
    combining the first, second, and third sub-indices to compile at least one composite index from the sub-indices indicative of a current state of the patient's heart and suitable for use in evaluating cardiac health risks in the patient.

2. A method according to claim 1, further comprising the step of measuring ECG data from the patient, wherein the first, second and third sub-indices are determined based on the EGG data.

3. A method according to claim 1, wherein the step of determining said first sub-index is further defined as determining the level of non-linear behavior found in the heart rate variability of the patient.

4. A method according to claim 1, wherein the step of determining the second sub-index includes the steps of:
    analyzing the repolarisation phase of the physiological functioning of the heart of the patient;
    determining a set of repolarisation parameters based on the analyzing step; and
    providing the second sub-index from the set of repolarization parameters.

5. A method according to claim 4, wherein the step of determining the second sub-index further includes the step of calculating the second sub-index as a weighted sum of at least some of the repolarisation parameters.

6. A method according to claim 1, wherein the third sub-index is determined based on the current extent of ventricular arrhythmia occurring in the heart of the patient.

7. A method according to claim 1, wherein the third sub-index is determined based on the current extent of ventricular arrhythmia occurring in the heart of the patient and an analysis of the electrical conduction functioning of the heart.

8. A method according to claim 1, wherein the composite index is determined as a weighted sum of the first, second, and third sub-indices.

9. A method according to claim 1, further defined as repeating the steps of the method to provide a plurality of sequentially obtained composite indices.

10. A method according to claim 9, further comprising the steps of
carrying out a comparison of composite indices; and
giving an alarm when the comparison of composite indices fulfills a predetermined condition.

11. A method according to claim 1, further comprising the steps of
determining at least one parameter relating to the arterial blood pressure of the patient; and
utilizing said at least one parameter in determining the second sub-index.

12. A method according to claim 1, further comprising the steps of
determining a value for the arterial blood oxyhemoglobin saturation of the patient; and
utilizing said value in determining the second sub-index.

13. A system providing a composite, multiple component index for assessing a current state of a patient's heart to evaluate associated cardiac health risks, the system comprising:
measurement means for obtaining ECG data from the patient;
first calculation means for determining a first sub-index from the medical data, the first sub-index indicating the current level of chaos in heart rate variability of the patient;
second calculation means for determining a second sub-index from the medical data, the second sub-index indicating the current energy level in the myocardium of the patient;
third calculation means for determining a third sub-index from the medical data, the third sub-index indicating the current degree of arrhythmia of the patient; and
fourth calculation means for combining the first, second, and third sub-indices to compile at least one composite index from the sub-indices.

14. A system according to claim 13, wherein the measurement means are configured to provide, in addition to the ECG data, blood pressure data related to the patient.

15. A system according to claim 13, wherein the system further comprises a communication interface operatively connected to said fourth calculation means, for connecting the system to an external device.

16. A system according to claim 13, wherein the first, second, third, and fourth calculation means reside in a single processor unit.

* * * * *